United States Patent [19]

Tzikas et al.

[11] Patent Number: 4,997,937
[45] Date of Patent: Mar. 5, 1991

[54] FIBER-REACTIVE DIOXAZINE DYES CONTAINING TWO VINYLSULFONYL MOIETIES

[75] Inventors: Athanassios Tzikas, Pratteln; Peter Aeschlimann, Allschwil, both of Switzerland

[73] Assignee: Ciba-Geigy Corporation, Ardsley, N.Y.

[21] Appl. No.: 422,339

[22] Filed: Oct. 16, 1989

[30] Foreign Application Priority Data

Oct. 18, 1988 [CH] Switzerland .......... 3877/88-0

[51] Int. Cl.$^5$ .......................................... C09B 19/02
[52] U.S. Cl. .................................. 544/77; 544/76; 544/99; 534/617; 564/163
[58] Field of Search .............. 534/617; 544/99, 76, 544/77

[56] References Cited

U.S. PATENT DOCUMENTS

| | | | |
|---|---|---|---|
| 2,020,651 | 11/1955 | Kalischer et al. | 544/99 X |
| 4,622,396 | 11/1986 | Harms et al. | 544/76 |
| 4,766,206 | 8/1988 | Tzikas | 534/619 |
| 4,841,028 | 6/1989 | Aeschilmann et al. | 534/617 X |

FOREIGN PATENT DOCUMENTS

| | | | |
|---|---|---|---|
| 0210951 | 2/1987 | European Pat. Off. | 534/618 |
| 296411 | 12/1988 | European Pat. Off. | 544/99 |
| 3628084 | 3/1988 | Fed. Rep. of Germany | 544/99 |

*Primary Examiner*—Floyd D. Higel
*Assistant Examiner*—Fiona T. Powers
*Attorney, Agent, or Firm*—George R. Dohmann; Edward McC. Roberts

[57] ABSTRACT

Dyes suitable for dyeing and printing cellulose-containing fiber materials which produce blue dyeings and prints having good fastness properties. These dyes are of the formula

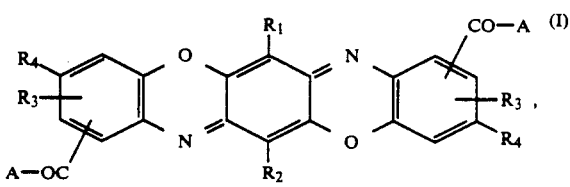

wherein $R_1$ and $R_2$ are each independently of the other hydrogen, halogen, $C_1$-$C_4$alkyl, $C_1$-$C_4$alkoxy, phenoxy, carboxyl carbamoyl or $C_1$-$C_4$alkanoylamino; $R_3$ is hydrogen, sulfo, $C_1$-$C_4$alkyl, $C_1$-$C_4$alkoxy, halogen, carboxyl, carbamoyl, N-$C_1$-$C_4$alkylcarbamoyl, N,N-di-$C_1$-$C_4$alkylcarbamoyl, $C_1$-$C_4$alkylsulfonyl, sulfamoyl, N-$C_1$-$C_4$alkylsulfamoyl or N,N-di-$C_1$-$C_4$alkylsulfamoyl; $R_4$ is a radical of the formula

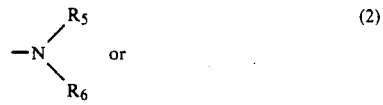

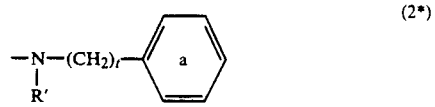

$R_5$ and $R_6$ are independently of each other hydrogen or unsubstituted or hydroxyl-, sulfo-, sulfato-, carboxyl-, cyano-, halogen-, $C_1$-$C_4$alkoxycarbonyl-, $C_1$-$C_4$alkanoyloxy- or carbamoyl-substituted and uninterrupted or, except in the case of methyl, —O—, —S— or —N—H—interrupted $C_1$-$C_6$alkyl; R' is hydrogen or $C_1$-$C_6$alkyl; t is an integer from 0 to 4; the phenyl radical (a) is unsubstituted or substituted by $C_1$-$C_4$alkyl, $C_1$-$C_4$alkyl substituted by hydroxyl-, sulfo or sulfato, $C_1$-$C_4$alkoxy, halogen, sulfo, carboxyl or hydroxy, and A is a radical of the formula

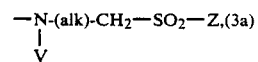

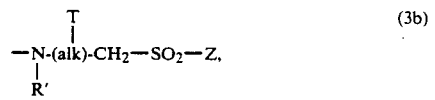

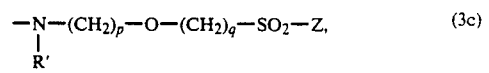

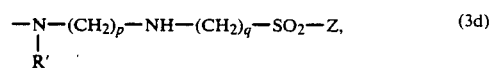

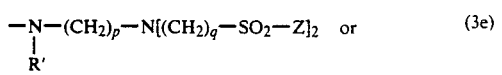

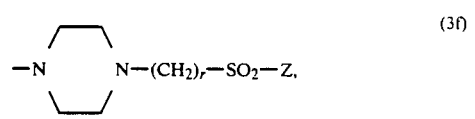

where R' is as defined above, (alk) is $C_1$-$C_6$alkylene, T is hydrogen, halogen, hydroxyl, sulfato, carboxyl, cyano, $C_1$-$C_4$alkanoyloxy, $C_1$-$C_4$alkoxycarbonyl, carbamoyl or a radical —$SO_2$—Z, V is hydrogen, substituted or unsubstituted $C_1$-$C_4$alkyl or a radical of the formula -(alk)—$CH_2$—$SO_2$—Z, where (alk) is as defined above, Z is a radical of the formula —CH=$CH_2$ *or* —$CH_2$—$CH_2$—Y, Y is a leaving group selected from the group consisting of —$OSO_3H$, —$SSO_3H$, —O-$COCH_3$, —OCO—$C_6H_5$, $OPO_3H_2$, —Cl, Br, —F, (Abstract continued on next page.)

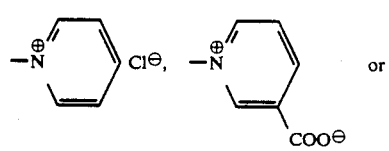, or 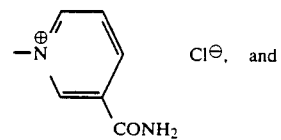
p, q and r are each independently of the others an integer from 1 to 6.
14 Claims, No Drawings

FIBER-REACTIVE DIOXAZINE DYES CONTAINING TWO VINYLSULFONYL MOIETIES

Reactive dyes have long been widely used for the dyeing and printing of textiles made of fibre materials, and today there are a large number of usable reactive dyes available having different properties for various applications. Yet, compared with the ever higher standards required of reactive dyeings in terms of economy, convenience of application and fastness levels, the level of technical performance which has been reached is frequently not fully satisfactory.

For instance, it is frequently found that the degree of fixation is too low and that the difference between the degree of exhaustion and degree of fixation is too large (high hydrolysis loss), so that an appreciable portion of reactive dye is lost for dyeing. Furthermore, the build-up potential frequently leaves something to be desired.

It is an object of the present invention to find new improved reactive dyes which show high reactivity and a good build-up potential, which can be dyed with a high yield of fixation, which is suitable in particular for the exhaust method, and which produce wet-and light-fast dyeings on cellulose-containing fibre material.

It has been found that the novel reactive dyes defined hereinafter meet these requirements.

The present invention accordingly provides compounds of the formula (I)

where $R_1$, $R_2$ and $R_3$ are each independently of the others hydrogen or a substituent, $R_4$ is a radical of the formula $$-N\begin{matrix}R_5\\R_6\end{matrix} \quad (2)$$

$$-N(CH_2)_t-\text{(a)} \quad (2^*)$$
$$\phantom{-N}|\phantom{(CH_2)_t-(a)}$$
$$\phantom{-N}R'$$

where $R_5$ and $R_6$ are each independently of the other hydrogen or substituted or unsubstituted $C_1-C_6$alkyl, $R'$ is hydrogen or $C_1-C_6$alkyl, t is an integer from 0 to 4 and the phenyl radical (a) may be substituted, and A is a radical of the formula $$-N\text{-(alk)-}CH_2-SO_2-Z, \quad (3a)$$
$$\phantom{-N}|$$
$$\phantom{-N}V$$

$$\phantom{-}T \quad (3b)$$
$$\phantom{-}|$$
$$-N\text{-(alk)-}CH_2-SO_2-Z,$$
$$\phantom{-N}|$$
$$\phantom{-N}R'$$

$$-N-(CH_2)_p-O-(CH_2)_q-SO_2-Z, \quad (3c)$$
$$\phantom{-N}|$$
$$\phantom{-N}R'$$

$$-N-(CH_2)_p-NH-(CH_2)_q-SO_2-Z, \quad (3d)$$
$$\phantom{-N}|$$
$$\phantom{-N}R'$$

$$-N-(CH_2)_p-N[(CH_2)_q-SO_2-Z]_2 \text{ or} \quad (3e)$$
$$\phantom{-N}|$$
$$\phantom{-N}R'$$

$$-N\diagdown\diagup N-(CH_2)_r-SO_2-Z, \quad (3f)$$

where $R'$ is as defined above, (alk) is a $C_1-C_6$alkylene radical, T is hydrogen, halogen, hydroxyl, sulfato, carboxyl, cyano, $C_1-C_4$alkanoyloxy, $C_1-C_4$alkoxycarbonyl, carbamoyl or a radical $-SO_2-Z$, V is hydrogen, substituted or unsubstituted $C_1-C_4$alkyl or a radical of the formula $-(alk)-CH_2-SO_2-Z$, where (alk) is as defined above, Z is a radical of the formula $-CH=CH_2$ or $-CH_2-CH_2-Y$, Y is a leaving group, and p, q and r are each independently of the others an integer from 1 to 6.

The radicals $R_1$ and $R_2$ are, for example, hydrogen, halogen such as bromine and in particular chlorine, $C_1-C_4$alkyl, which is generally to be understood as meaning methyl, ethyl, n- or iso-propyl, or n-, sec- or tert-butyl, $C_1-C_4$alkoxy, which generally encompasses methoxy, ethoxy, n- or isopropoxy or n-, iso- or tert-butoxy, phenoxy, carboxyl, carbamoyl or $C_1-C_4$alkanoylamino, e.g. acetylamino.

Preferably, $R_1$ and $R_2$ are each hydrogen, methyl, methoxy, acetylamino or, particularly preferably, chlorine.

$R_3$ is for example hydrogen, sulfo, $C_1-C_4$alkyl, $C_1-C_4$alkoxy, halogen, carboxyl, carbamoyl, N-$C_1-C_4$alkylcarbamoyl, N,N-di-$C_1-C_4$alkylcarbamoyl, $C_1-C_4$alkylsulfonyl, sulfamoyl, N-$C_1-C_4$alkylsulfamoyl or N,N-di-$C_1-C_4$alkylsulfamoyl.

Preferably, $R_3$ is hydrogen, chlorine, $C_1-C_4$alkyl or $C_1-C_4$alkoxy, but particularly preferably hydrogen.

A preferred embodiment of the invention relates to compounds of the formula (1) where $R_1$ and $R_2$ are each chlorine and $R_3$ is hydrogen.

Substituted or unsubstituted $C_1-C_6$alkyl $R_5$ and/or $R_6$ in formula (2) is for example methyl, ethyl, n-propyl, isopropyl, n-butyl, sec-butyl, tert-butyl or straight-chain or branched pentyl or hexyl, which may each be substituted, for example by hydroxyl, sulfo, sulfato, carboxyl, cyano, halogen, $C_1-C_4$alkoxycarbonyl, $C_1-C_4$alkanoyloxy or carbamoyl and alkyl, except methyl, may additionally be interrupted by for example $-O-$, $-S-$ or $-NH-$.

Preferably, one of $R_5$ and $R_6$ is hydrogen and the other is $C_1-C_6$alkyl which may be substituted as described above and/or interrupted by $-O-$, $-S-$ or $-NH-$.

$R_4$ can be for example of the formula $$-N\text{-alk-}U, \quad (2a)$$
$$\phantom{-N}|$$
$$\phantom{-N}R'$$

$$-N[(alk)-U]_2, \quad (2b)$$

$$-NH-(CH_2)_p-O-(CH_2)_q-U, \quad (2c)$$

-continued $$-NH-(CH_2)_p-NH-(CH_2)_q-U \text{ or} \quad (2d)$$

$$\begin{array}{c} U \\ | \\ -NH-(CH_2)\text{-(alk)-}CH_2-U \end{array} \quad (2e)$$

where R', (alk), p and q are as defined above and U is hydroxyl, sulfo, sulfato, carboxyl, cyano, halogen, $C_1$-$C_4$alkoxycarbonyl, e.g. methoxycarbonyl or ethoxycarbonyl, $C_1$-$C_4$alkanoylamino, in particular acetylamino or propionylamino, or carbamoyl.

R' is for example hydrogen, methyl, ethyl, n-propyl, isopropyl, n-butyl, sec-butyl or tert-butyl or straight-chain or branched pentyl or hexyl. Preferably, R' is hydrogen, methyl or ethyl but particularly preferably hydrogen.

(alk) in the formulae (2a), (2b) and (2e) is for example, methylene, ethylene, 1,3-propylene, 1,4-butylene, 1,5-pentylene or 1,6-hexylene or a branched isomer thereof. Preferably, (alk) is $C_1$-$C_4$alkylene, especially methylene or ethylene.

p and q in the formulae (2c) and (2d) are preferably, independently of each other, an integer from 1 to 4; particularly preferably, p and q are each 2.

U in the formulae (2a) to (2e) is preferably hydroxyl, sulfo or sulfato, but particularly preferably sulfato.

A preferred embodiment of the present invention relates to compounds of the formula (1) where $R_4$ is a radical of the formula $$\begin{array}{c} R'' \\ | \\ -N\text{-(alk')-}U', \end{array} \quad (2a')$$

$$-N[(alk')\text{-}U']_2, \quad (2b')$$

$$-NH-CH_2-CH_2-O-CH_2-CH_2-U', \quad (2c')$$

$$-NH-CH_2-CH_2-NH-CH_2-CH_2-U' \text{ or} \quad (2d')$$

$$\begin{array}{c} -NH-CH_2\text{-(alk')-}CH_2-U' \\ | \\ U' \end{array} \quad (2e)$$

where R" is hydrogen, methyl or ethyl, (alk') is $C_1$-$C_4$alkylene and U is hydroxyl, sulfo or sulfato.

Examples of particularly preferred radicals $R_4$ are:

$$-NH-(CH_2)_2-OSO_3H,$$

$$-NH-(CH_2)_3-OSO_3H,$$

$$-NH-(CH_2)_4-OSO_3H,$$

$$\begin{array}{c} -N-(CH_2)_2-OSO_3H, \\ | \\ CH_3 \end{array}$$

$$\begin{array}{c} CH_3 \\ | \\ -NH-CH_2-CH_2-CH-OSO_3H, \end{array}$$

$$\begin{array}{c} CH_3 \\ | \\ -NH-C-CH_2-OSO_3H, \\ | \\ CH_3 \end{array}$$

$$-NH-CH_2-CH_2-O-CH_2-CH_2-OSO_3H,$$

$$-NH-CH_2-CH_2-NH-CH_2-CH_2-OSO_3H,$$

-continued
$$\begin{array}{c} OSO_3H \\ | \\ -NH-CH_2-CH-CH_2-OSO_3H. \end{array}$$

In a radical $R_4$ of the formula (2*), R' is subject to the above-indicated definitions and preferences; t is preferably 1 or 2.

Suitable substituents on the phenyl radical (a) are for example unsubstituted or hydroxyl-, sulfo- or sulfato-substituted $C_1$-$C_4$alkyl, $C_1$-$C_4$alkoxy, halogen, sulfo, carboxyl and hydroxyl.

The phenyl radical (a) is preferably unsubstituted or for example substituted by sulfo, methyl and/or methoxy.

In a radical $R_4$ of the above-indicated formula (2*), preferably R' is hydrogen, t is 1 or 2 and the phenyl radical (a) is unsubstituted or sulfo-, methyl-and/or methoxy-substituted.

In the formulae (3a) to (3f), R', (alk), p and q are subject to the abovementioned definitions and preferences.

T is preferably hydrogen, hydroxyl, sulfato, acetyloxy, carboxyl, methoxycarbonyl, ethoxycarbonyl or $-SO_2-Z$, where Z is a defined above; T is particularly preferably hydrogen or $-SO_2-Z$.

Substituted $C_1$-$C_4$alkyl V can be for example halogen-, hydroxyl-, cyano-, carboxyl-, sulfo-, sulfato-, $C_1$-$C_4$alkoxy- or $C_1$-$C_4$alkoxycarbonyl-substituted $C_1$-$C_4$alkyl.

Examples of substituted $C_1$-$C_4$alkyl are: carboxymethyl, β-carboxyethyl, methoxycarbonylmethyl, ethoxycarbonylmethyl, β-carboxyethyl, methoxycarbonylmethyl, ethoxycarbonylmethyl, β-methoxyethyl, β-ethoxyethyl, β-chloroethyl, γ-bromopropyl, β-hydroxyethyl, β-hydroxybutyl, β-cyanoethyl, sulfomethyl, β-sulfoethyl, β-sulfatoethyl.

A radical V of the formula $Z-O_2S-H_2C-$(alk)- can be different from the second radical $Z-O_2S-H_2C-$(alk)- in the formula (3a) or, preferably, be identical thereto.

V is preferably hydrogen, methyl, ethyl or $Z-O_2S-H_2C$(alk)-; V is most preferably hydrogen.

Y is for example an inorganic or organic radical which is detachable under alkaline conditions.

Examples of suitable radicals Y are:

$-OSO_3H$, $-SSO_3H$, $-OCOCH_3$, $-OCO-C_6H_5$, $OPO_3H_2$, $-Cl$, $Br$, $-F$,

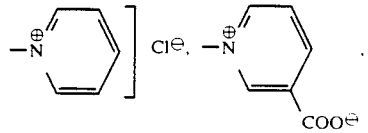

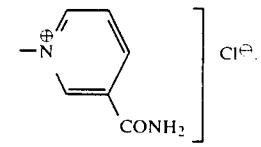

Preferably, Y is $-OSO_3H$, $-SSO_3H$, $-OCOCH_3$, $-OPO_3H_2$ or $-Cl$, but in particular $-OSO_3H$.

r in the formula (3e) is preferably an integer from 1 to 4, particularly preferably 2 or 3.

A preferably conforms to the formula $$-N(\text{alk}')-CH_2-SO_2-Z', \quad (3a')$$
$$\phantom{-N(alk)}| \phantom{-CH_2-SO_2-Z,}$$
$$\phantom{-N(alk)-CH_2-SO_2-Z,}V'$$

$$\begin{array}{c} SO_2-Z' \\ | \\ -NH-(\text{alk}')-CH_2-SO_2-Z', \end{array} \quad (3b')$$

$$-NH-CH_2-CH_2-O-CH_2-CH_2-SO_2-Z', \quad (3c')$$

$$-NH-CH_2-CH_2-NH-CH_2-CH_2-SO_2-Z' \text{ or} \quad (3d')$$

$$-N\underset{\diagdown\underline{\phantom{xx}}\diagup}{\overset{\diagup\overline{\phantom{xx}}\diagdown}{\phantom{x}}}N-(CH_2)_{\overline{2-3}}-SO_2-Z', \quad (3f')$$

where V' is hydrogen, methyl, ethyl or -(alk')—CH$_2$—SO$_2$—Z', (alk') is C$_1$-C$_4$alkylene, Z' is vinyl or —CH$_2$—CH$_2$—Y', and Y' is —OSO$_3$H, —SSO$_3$H, —O-COCH$_3$, —OPO$_3$H$_2$ or —Cl.

Examples of particularly preferred radicals A are:

$$-NH-(CH_2)_2-SO_2-(CH_2)_2-OSO_3H$$

$$-NH-(CH_2)_3-SO_2-(CH_2)_2-OSO_3H$$

$$-NH-(CH_2)_2-O-(CH_2)_2-SO_2-(CH_2)_2-OSO_3H$$

$$-N[-(CH_2)_2-SO_2-(CH_2)_2-OSO_3H]_2$$

$$\begin{array}{c}-N-(CH_2)_2-SO_2-(CH_2)_2-OSO_3H \\ | \\ CH_3\end{array}$$

$$\begin{array}{c}-N-(CH_2)_2-SO_2-(CH_2)_2-OSO_3H \\ | \\ C_2H_5\end{array}$$

$$\begin{array}{c}SO_2-(CH_2)_2-OSO_3H \\ | \\ -NH-CH_2-CH-CH_2-CH_2-CH_2-SO_2-(CH_2)_2-OSO_3H\end{array}$$

$$-N\underset{\diagdown\underline{\phantom{xx}}\diagup}{\overset{\diagup\overline{\phantom{xx}}\diagdown}{\phantom{x}}}N-(CH_2)_3-SO_2-(CH_2)_2-OSO_3H$$

A preferred group of dyes according to the invention comprises compounds of the formula (1) where R$_1$ and R$_2$ are each chlorine, R$_3$ is hydrogen, R$_4$ is a radical of the above-indicated formula (2a), (2b), (2c), (2d) or (2e), and A is a radical of the above-indicated formula (3a'), (3b'), (3c'), (3d') or (3f').

Particular preference is given to reactive dyes of the formula (1) where R$_1$ and R$_2$ are each chlorine, R$_3$ is hydrogen, R$_4$ is a radical of the above-indicated formula (2a'), (2b'), (2c'), (2d') or (2e'), and A is a radical of the formula $$-NH-(CH_2)_2-SO_2-(CH_2)_2-OSO_3H,$$

$$-NH-(CH_2)_3-SO_2-(CH_2)_2-OSO_3H,$$

$$-NH-(CH_2)_2-O-(CH_2)_2-SO_2-(CH_2)_2-OSO_3H,$$

$$-N[(CH_2)_2-SO_2-(CH_2)_2-OSO_3H]_2,$$

$$\begin{array}{c}-N-(CH_2)_2-SO_2-(CH_2)_2-OSO_3H, \\ | \\ CH_3\end{array}$$

$$\begin{array}{c}-N-(CH_2)_2-SO_2-(CH_2)_2-OSO_3H, \\ | \\ C_2H_5\end{array}$$

$$\begin{array}{c}SO_2-(CH_2)_2-OSO_3H \\ | \\ -NH-CH_2-CH-CH_2-CH_2-CH_2-SO_2-(CH_2)_2-OSO_3H \text{ or}\end{array}$$

$$-N\underset{\diagdown\underline{\phantom{xx}}\diagup}{\overset{\diagup\overline{\phantom{xx}}\diagdown}{\phantom{x}}}N-(CH_2)_3-SO_2-(CH_2)_2-OSO_3H.$$

A further group of preferred reactive dyes are compounds of the formula (1) where R$_1$ and R$_2$ are each chlorine, R$_3$ is hydrogen, R$_4$ is a radical of the formula (2*), where R' is hydrogen and t is 1 or 2, and the phenyl radical (a) is unsubstituted or sulfo-, methyl- and/or methoxy-substituted, and A is subject to the above-indicated definitions and preferences.

The compounds of the formula (1) can be obtained in a manner known per se, for example by condensing an amine of the formula $$\underset{H_2N}{\phantom{x}}\underset{\phantom{x}}{\overset{CO-A_1}{\bigcirc}}\underset{R_4}{\overset{R_3}{\phantom{x}}} \quad (4)$$

where R$_3$ and R$_4$ are as defined above and A$_1$ is A or a radical of the above-indicated formula (3a) to (3f), where Z is —CH$_2$—CH$_2$—OH, with a 1,4-benzoquinone of the formula $$\underset{R_2}{\overset{Q_1}{\bigcirc}}\underset{O}{\overset{R_1}{\bigcirc}}Q_2 \quad (5)$$

where R$_1$ and R$_2$ are as defined above and Q$_1$ and Q$_2$ are each hydrogen, chlorine, bromine, C$_1$-C$_4$alkoxy or phenoxy, to give a compound of the formula (6)

converting the resulting anil compound by subsequent ring closure to a dioxazine compound, and if necessary converting the radical A$_1$ into a radical A.

The condensation of the amines of the formula (4) with the benzoquinones of the formula (5) is advantageously carried out in an aqueous or aqueous organic medium in the presence of alkaline condensing agents at pH 3-11, preferably pH 4-8, and temperatures of 20° to 100° C., preferably 30°-60° C., or in buffered solutions which contain the above alkaline condensation products. It is also possible to work in a purely organic medium in the presence of acid-binding agents.

Alkaline condensing agents are for example sodium bicarbonate, sodium carbonate, sodium acetate, potassium acetate, sodium hydroxide, potassium hydroxide, sodium phosphates and sodium borate.

The compounds of the formula (4) are novel and constitute a further part of the subject-matter of the present invention. They can be prepared, for example, by first reacting a compound of the formula

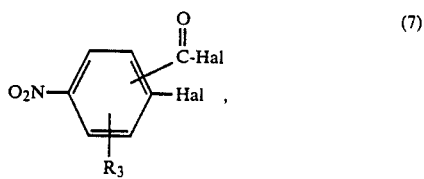

where $R_3$ is as defined above, and Hal is halogen, in particular chlorine, with an amine of the formula

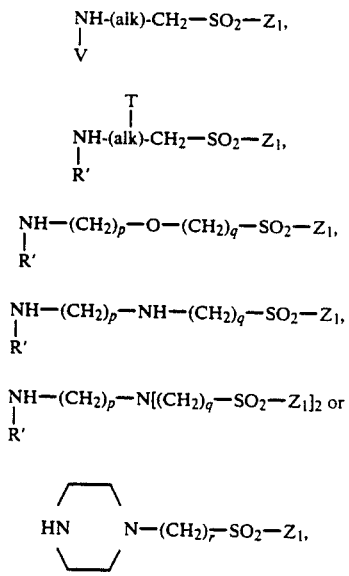

where (alk), V, T, R', p, q and r are each as defined above and $Z_1$ is Z or —$CH_2$—$CH_2$—OH, and then with a amine of the formula

where $R_5$ and $R_6$ are each as defined above, reducing the nitro group to an amino group and if necessary converting $Z_1$ into Z by introducing a leaving group Y.

In a modification of the above-described process, it is possible to use in place of the nitro compound of the formula (7) the corresponding amino compound, thereby eliminating the need to reduce the nitro group. The nitro compounds of the formula (7) as well as the corresponding amino compounds are known per se or can be obtained by known methods.

A further variant of the above-described process comprises using in place of the amines of the formulae ($3a_1$) to ($3f_1$) suitable intermediates and subsequently converting the latter into the corresponding amines.

Suitable intermediates are for example the thioetheramines which are analogous to the formulae ($3a_1$) to ($3f_1$) and which after the reaction with a compound of the formula (7) can be oxidized to the corresponding sulfones in a conventional manner.

It is also possible first to react suitable haloalkylamines with the acid chloride of the formula (7) and to react the resulting compounds with 2-mercaptoethanol and sodium alcoholate in alcohol to give the abovementioned thioetheramines, which can subsequently be oxidized in turn to the sulfones of the formulae ($3a_1$) to ($3f_1$).

Preference is given to using those amines of the formulae ($3a_1$) to ($3f_1$), or intermediates therefor, which contain a preliminary stage of the reactive radical and in which accordingly $Z_1$ is for example a radical of the formula HO—$H_2$C—$H_2$C. The preliminary stage of the reactive radical is then subsequently converted into the final stage as described hereinafter.

The amines of the formulae ($3a_1$) to ($3f_1$) and intermediates therefor are known for example from EP-A-210,951, or can be prepared in a similar manner.

The reaction (condensation) of the acid chloride of the formula (7) with the aforementioned amines is carried out for example in an aqueous, aqueous organic or organic medium at a temperature between about 0° and 120° C., preferably 10° to 60° C., in the presence of alkaline acid-binding agents, for example alkali metal hydroxides, carbonates or bicarbonates.

Starting from intermediates for amines of the formulae ($3a_1$) to ($3f_1$), the oxidation of the thioether compounds to give sulfones can be carried out by various methods, for example with hydrogen peroxide in the presence or absence of tungsten or vanadium compounds as catalysts, also with peracetic acid, potassium permanganate or chromic acid, or with chlorine/hydrochloric acid, in each case in an aqueous, aqueous organic or organic medium.

The nitro group is reduced to an amino group in a manner known per se by catalytic hydrogenation with Pd/carbon in ethanol, ethyl acetate or tetrahydrofuran at room temperature up to about 40° C. The reduction can also be carried out with Fe/hydrochloric acid or Fe/acetic acid in aqueous solution.

The carboxamides thus obtainable, in which the grouping —$SO_2$—$Z_1$ is a β-hydroxyethylsulfonyl group, can be converted by treatment with sulfating agents, phosphorylating agents, halogenating agents, alkyl- or aryl-sulfonyl halides, alkyl- or aryl-carbonyl halides or alkyl- or aryl-carboxylic anhydrides into the corresponding dye intermediates in which the grouping —$SO_2$—$Z_1$ is for example —$SO_2$—$CH_2$—$CH_2$—O—$SO_3H$, —$SO_2$—$CH_2$—$CH_2$—O—$PO_3H_2$, —$SO_2$—$CH_2$—$CH_2$—halogen, —$SO_2$—$CH_2$—$CH_2$—O—CO—$CH_3$ or —$SO_2$—$CH_2$—$CH_2$—O—CO—$C_5H_5$. The products thus obtained can in turn be converted by treatment with alkaline agents, for example alkali metal hydroxide or alkali metal carbonate, such as sodium hydroxide or sodium carbonate, into corresponding compounds in which the grouping —$SO_2$—$Z_1$ is —$SO_2$—CH=$CH_2$. The products thus obtained can in turn be converted by reaction (addition) with salts of thiosulfuric acid, such as sodium thiosulfate, into compounds in which the grouping —$SO_2$—$Z_1$ is —$SO_2$—$CH_2$—$CH_2$—S—$SO_3H$.

Suitable sulfating agents here are for example concentrated sulfuric acid, also chlorosulfuric acid, amidosulfuric acid and other sulfur trioxide donor compounds. Suitable phosphorylating agents here are for example concentrated phosphoric acid, pyrophosphoric, metaphosphoric or polyphosphoric acid, alkyl polyphosphates, phosphoryl chloride, or mixtures of phosphoric acid and phosphorus(V) oxide. Suitable halogenating agents are for example thionyl chloride and thionyl bromide.

Substituents and alkyls $R_5$ and/or $R_6$ of amino substituent $R_4$ may already be present in the parent amine of the formula (2') or, however, may be introduced in a conventional manner not until after the synthesis has taken place. It is also conceivable subsequently to replace a substituent present in the starting material of the formula (2') for another substituent, an example of such a replacement reaction being the replacement of hydroxyl by sulfato by means of suitable sulfating agents as mentioned above.

The compounds of the formulae (2') and (5) are known or can be obtained by methods known per se.

The ring closure of the anil compound of the formula (6) to give a dioxazine compound can be carried out by methods known per se, in particular in concentrated sulfuric acid and especially in oleum having $SO_3$ contents of 1–50% by weight at temperatures of 10° to 80° C., in the presence or absence of oxidizing agents such as potassium peroxodisulfate, ammonium peroxodisulfate, magnesium oxide or organic peroxides. Preferably, hydroxyalkyl present in the starting materials, for example as $\beta$-hydroxyethylsulfonyl, is converted under the ring closure reaction conditions into the corresponding sulfatoalkyl; in the case of $\beta$-sulfatoethylsulfonyl, it may subsequently be converted as described above into the vinyl form or into another one of the abovementioned preliminary stages of vinylsulfonyl.

The most important versions of the process are illustrated in the Examples.

The dyes of the formula (1) according to the invention are fibre-reactive. Fibre-reactive dyes for the purposes of the present invention are those which are capable of reacting with the hydroxyl groups of the cellulose or with the reactive centres of natural or synthetic polyamides to form covalent chemical bonds.

The reactive dyes of the formula (1) according to the invention are suitable for dyeing and printing a wide range of materials, such as silk, leather, wool, polyamide fibres and in particular cellulose-containing fibre materials of any kind. Such fibre materials are for example the natural cellulose fibres, such as cotton, linen and hemp, and also pulp and regenerated cellulose. The reactive dyes according to the invention are also suitable for dyeing or printing hydroxyl-containing fibres present in blend fabrics, for example blends of cotton with polyester fibres or polyamide fibres.

The dyes according to the invention can be applied to and fixed on the fibre in various ways, in particular in the form of aqueous dye solutions and print pastes. They are suitable not only for the exhaust method but also for dyeing by the padding method whereby the fibre material is impregnated with aqueous dye solutions in the presence or absence of salt and the dyes are fixed after an alkali treatment or in the presence of alkali with or without heating. They are particularly suitable for the cold pad-batch process, whereby the dye is applied on a pad mangle together with the alkali and is then fixed by storage at room temperature for several hours. After fixation, the dyeings or prints are thoroughly rinsed with cold and hot water in the presence or absence of an agent which acts as a dispersant and promotes the diffusion of the unfixed portions.

The reactive dyes according to the invention are notable for high reactivity, good fixing properties and good build-up potential. They can therefore be used in exhaust dyeing at low dyeing temperatures, and only require short steam times in the pad-steam process. The degrees of fixation are high, and the unfixed portions are readily washed off, the difference between the degree of exhaustion and the degree of fixation being remarkably small; that is, the loss by hydrolysis being very small. The reactive dyes according to the invention are also suitable in particular for printing, in particular on cotton, but also for printing nitrogen-containing fibres, for example wool or silk or blend fabrics which contain wool or silk.

The dyeings and prints prepared with the dyes according to the invention on cellulose fibre materials show high colour strength and a high fibre-dye bond stability not only in the acid but also in the alkaline range and also good light fastness and very good wet fastness properties, such as wash, water, sea water, cross-dyeing and perspiration fastness properties, and also good pleating fastness, hot press fastness and rub fastness. Another noteworthy aspect is the very good chlorine fastness of the reactive dyes according to the invention.

The Examples which follow will illustrate the invention. The temperatures are given in degrees Celsius. Parts and percentages are by weight, unless otherwise stated. Parts by weight bear the same relation to parts by volume as the kilogram to the liter.

EXAMPLE 1

66.5 parts of the amine of the formula

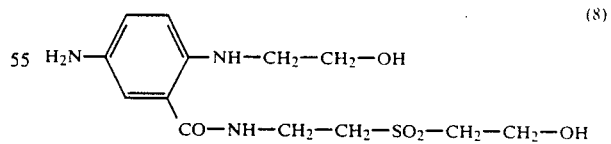

(8)

are suspended in 600 parts of water, and the pH of the suspension is adjusted to 6.0. 24.6 parts of 2,3,5,6-tetrachloroquinone and 80 parts of methanol are added, the batch is heated to about 40° C., and the pH is maintained at 5.8 to 6.0 by the addition of sodium carbonate solution. After the reaction has ended, the precipitated product is filtered off with suction, washed with water and dried. It conforms to the formula

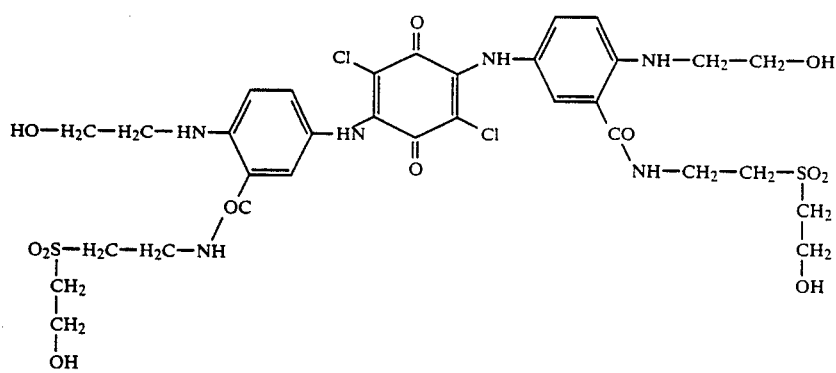

EXAMPLE 2

83 parts of the chloranil condensation product obtained as described in Example 1 are added to 200 parts of 20% oleum at 10° to 20° C. in the course of about an hour. The mixture is subsequently stirred for about 30 to 60 minutes, and 45 parts of potassium peroxodisulfate are then added at 20° to 25° C. with slight external cooling in the course of about 45 minutes. After stirring for 1 hour, the reaction mixture is discharged onto 1500 parts of ice and the resulting clear blue solution is initially admixed with 7.5 parts of trisodium phosphate and then with 4N sodium hydroxide solution by stirring and cooling until a pH of 4.5 to 5.0 is obtained. The precipitated dye is filtered off with suction, wahsed and dried under reduced pressure; it conforms to the formula

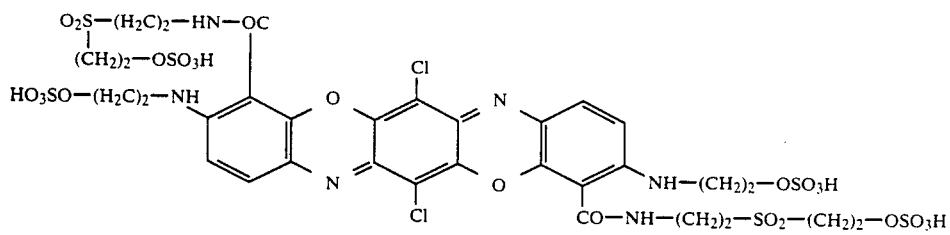

and dyes cotton in deep blue shades having excellent allround fastness properties.

EXAMPLES 3 to 31

The procedure of Examples 1 and 2 is followed except that the amine of the formula (8) is replaced by equivalent amounts of the amines indicated in the Table below, affording similar dyes which each dye cotton in a blue shade having good allround fastness properties.

| Example No. | Amine |
|---|---|
| 3 | $H_2N\text{-}C_6H_3(\text{NH-}(CH_2)_3\text{-OH})\text{-CO-NH-}(CH_2)_2\text{-SO}_2\text{-}(CH_2)_2\text{-OH}$ |
| 4 | $H_2N\text{-}C_6H_3(\text{NH-}CH_2\text{-}CH_2\text{-}CH(CH_3)\text{-OH})\text{-CO-NH-}(CH_2)_3\text{-SO}_2\text{-}(CH_2)_2\text{-OH}$ |
| 5 | $H_2N\text{-}C_6H_3(\text{NH-}CH_2\text{-}CH_2\text{-OH})\text{-CO-NH-}(CH_2)_2\text{-O-}(CH_2)_2\text{-SO}_2\text{-}(CH_2)_2\text{-OH}$ |

-continued

| Example No. | Amine |
|---|---|
| 6 | H₂N–C₆H₃(NH–(CH₂)₄–OH)–CO–N(CH₂–CH₂–SO₂–CH₂–CH₂–OH)₂ |
| 7 | H₂N–C₆H₃(NH–CH₂–CH₂–O–CH₂–CH₂–OH)–CO–NH–(CH₂)₂–SO₂–(CH₂)₂–OH |
| 8 | H₂N–C₆H₃(N(CH₃)–CH₂–CH₂–OH)–CO–NH–(CH₂)₂–SO₂–(CH₂)₂–OH |
| 9 | H₂N–C₆H₃(NH–CH₂–CH(OH)–CH₂–OH)–CO–N(piperazine)N–(CH₂)₃–SO₂–(CH₂)₂–OH |
| 10 | H₂N–C₆H₃(NH–C(CH₃)₂–CH₂–OH)–CO–NH–(CH₂)₂–SO₂–(CH₂)₂–OH |
| 11 | H₂N–C₆H₃(NH–CH₂–CH₂–OH)–CO–NH–CH₂–CH[(CH₂)₃–SO₂–(CH₂)₂–OH][SO₂–CH₂–CH₂–OH] |
| 12 | H₂N–C₆H₃(NH–CH₂–CH₂–OH)–CO–N(CH₃)–(CH₂)₂–SO₂–(CH₂)₂–OH |
| 13 | H₂N–C₆H₃(NH–(CH₂)₂–O–(CH₂)₂–OH)–CO–N(CH₂–CH₃)–(CH₂)₂–SO₂–(CH₂)₂–OH |
| 14 | H₂N–C₆H₃(NH–(CH₂)₂–NH–(CH₂)₂–OH)–CO–NH–(CH₂)₂–SO₂–(CH₂)₂–OH |

-continued

| Example No. | Amine |
|---|---|
| 15 | $H_2N$—[benzene]—NH—$CH_2$—[phenyl]<br>CO—NH—$(CH_2)_2$—$SO_2$—$(CH_2)_2$—OH |
| 16 | $H_2N$—[benzene]—NH—$CH_2$—[phenyl]—$SO_3H$<br>CO—NH—$(CH_2)_2$—$SO_2$—$(CH_2)_2$—OH |
| 17 | $H_2N$—[benzene]—NH—$CH_2$—[phenyl with $HO_3S$ and $SO_3H$]<br>CO—NH—$(CH_2)_2$—$SO_2$—$(CH_2)_2$—OH |
| 18 | $H_2N$—[benzene]—NH—$CH_2$—$CH_2$—[phenyl]<br>CO—NH—$(CH_2)_2$—$SO_2$—$(CH_2)_2$—OH |
| 19 | $H_2N$—[benzene]—NH—$CH_2$—$CH_2$—[phenyl]—$SO_3H$<br>CO—NH—$(CH_2)_2$—$SO_2$—$(CH_2)_2$—OH |
| 20 | $H_2N$—[benzene]—NH—$CH_2$—$CH_2$—[phenyl with $HO_3S$ and $SO_3H$]<br>CO—NH—$(CH_2)_2$—$SO_2$—$(CH_2)_2$—OH |
| 21 | $H_2N$—[benzene]—NH—$CH_2$—$CH_2$—$CH_2$—OH<br>CO—NH—$(CH_2)_2$—O—$(CH_2)_2$—$SO_2$—$(CH_2)_2$—OH |
| 22 | $H_2N$—[benzene]—NH—$CH_2$—CH(OH)—$CH_2$—OH<br>CO—NH—$(CH_2)_2$—O—$(CH_2)_2$—$SO_2(CH_2)_2$—OH |
| 23 | $H_2N$—[benzene]—NH—$CH_2$—$CH_2$—O—$CH_2$—$CH_2$—OH<br>CO—NH—$(CH_2)_2$—O—$(CH_2)_2$—$SO_2$—$(CH_2)_2$—OH |
| 24 | $H_2N$—[benzene]—NH—$CH_2$—$CH_2$—S—$CH_2$—$CH_2$—OH<br>CO—NH—$(CH_2)_2$—O—$(CH_2)_2$—$SO_2$—$(CH_2)_2$—OH |

-continued

| Example No. | Amine |
|---|---|
| 25 | H$_2$N—C$_6$H$_3$(NH—(CH$_2$)$_2$—OH)(CO—NH—(CH$_2$)$_4$—SO$_2$—(CH$_2$)$_2$—OH) |
| 26 | H$_2$N—C$_6$H$_3$(NH—(CH$_2$)$_2$—OH)(CO—NH—(CH$_2$)$_2$—NH—(CH$_2$)$_2$—SO$_2$—(CH$_2$)$_2$—OH) |
| 27 | H$_2$N—C$_6$H$_3$(NH—CH$_2$—CH(OH)—CH$_2$—OH)(CO—NH—(CH$_2$)$_2$—SO$_2$—(CH$_2$)$_2$—OH) |
| 28 | H$_2$N—C$_6$H$_3$(NH—CH$_2$—CH$_2$—SO$_3$H)(CO—NH—(CH$_2$)$_2$—SO$_2$—(CH$_2$)$_2$—OH) |
| 29 | H$_2$N—C$_6$H$_3$(NH—CH$_2$—CH$_2$—SO$_3$H)(CO—NH—(CH$_2$)$_2$—O—(CH$_2$)$_2$—SO$_2$—(CH$_2$)$_2$—OH) |
| 30 | H$_2$N—C$_6$H$_2$(CH$_3$)(NH—CH$_2$—CH$_2$—OH)(CO—NH—(CH$_2$)$_2$—SO$_2$—(CH$_2$)$_2$—OH) |
| 31 | H$_2$N—C$_6$H$_2$(Cl)(NH—CH$_2$—CH$_2$—OH)(CO—NH—(CH$_2$)$_2$—O—(CH$_2$)$_2$—SO$_2$—(CH$_2$)$_2$—OH) |

DYEING METHOD I 2 parts of the dye obtained as described in Example 1 are dissolved in 400 parts of water; 1500 parts of a solution containing 53 g of sodium chloride per liter are added. This dyebath is entered at 40° C. with 100 parts of a cotton fabric. After 45 minutes, 100 parts of a solution which contains 16 g of sodium hydroxide and 20 g of calcined calcium carbonate per liter are added. The temperature of the dyebath is maintained at 40° C. for a further 45 minutes. The dyed fabric is then rinsed, soaped off at the boil with a nonionic detergent for a quarter of an hour, rinsed once more and dried.

DYEING METHOD II 2 parts of the reactive dye obtained as described in Example 1 are dissolved in 400 parts of water; 1500 parts of a solution containing 53 g of sodium chloride per liter are added. This dyebath is entered at 35° C. with 100 parts of a cotton fabric. After 20 minutes, 100 parts of a solution which contains 16 g of sodium hydroxide and 20 g of calcined sodium carbonate per liter are added. The temperature of the dyebath is maintained at 35° C. for a further 15 minutes. The temperature is then raised to 60° C. in the course of 20 minutes. The temperature is maintained at 60° C. for a further 35 minutes. The fabric is then rinsed, soaped off at the boil with a nonionic detergent for a quarter of an hour, rinsed once more and dried.

DYEING METHOD III 8 parts of the reactive dye obtained as described in Example 1 are dissolved in 400 parts of water; 1400 parts of a solution containing 100 g of sodium sulfate per liter are added. This dyebath is entered at 25° C. with 100 parts of a cotton fabric. After 10 minutes, 200 parts of a solution containing 150 g of trisodium phosphate per liter are added. The temperature of the dyebath is then raised to 60° C. in the course of 10 minutes. The temperature is maintained at 60° C. for a further 90 minutes. The fabric is then rinsed, soaped off at the boil with a nonionic detergent for a quarter of an hour, rinsed once more and dried.

DYEING METHOD IV 4 parts of the reactive dye obtained as described in Example 1 are dissolved in 50 parts of water. 50 parts of a solution containing 5 g of sodium hydroxide and 20 g of calcined sodium carbonate per liter are added. The solution obtained is used to pad a cotton fabric in such a way that its weight increases by 70%, and the fabric is then wound onto a batching beam. The cotton fabric is stored in this state at room temperature for 3 hours. The dyed fabric is then rinsed, soaped off at the boil with a nonionic detergent for a quarter of an hour, rinsed once more and dried.

DYEING METHOD V 6 parts of the reactive dye obtained as described in Example 1 are dissolved in 50 parts of water. 50 parts of a solution containing 16 g of sodium hydroxide and 0.04 liter of 38° Bé water glass per liter are added. The solution obtained is used to pad a cotton fabric in such a way that its weight increases by 70%, the fabric is then wound onto a batching beam. The cotton fabric is stored in this state at room temperature for 10 hours. The dyed fabric is then rinsed, soaped off at the boil with a nonionic detergent for a quarter of an hour, rinsed once more and dried.

DYEING METHOD VI 2 parts of the reactive dye obtained as described in Example 1 are dissolved in 100 parts of water by the addition of 0.5 part of sodium m-nitrobenzenesulfonate. The solution obtained is used to impregnate a cotton fabric in such a way that its weight increases by 75%, and the fabric is then dried. The fabric is then impregnated with a 20° C. solution which contains 4 g of sodium hydroxide and 300 g of sodium chloride per liter, and squeezed off to a 75% weight increase, and the dyeing is steamed at 100° to 102° C. for 30 seconds, rinsed, soaped off at the boil with a 0.3% solution of a nonionic detergent for a quarter of an hour, rinsed and dried.

PRINTING METHOD I 3 parts of the reactive dye obtained as described in Example 1 are sprinkled with rapid stirring into 100 parts of stock thickening containing 50 parts of 5% sodium alginate thickening, 27.8 parts of water, 20 parts of urea, 1 part of sodium m-nitrobenzenesulfonate and 1.2 parts of sodium bicarbonate. The print paste thus obtained is used to print a cotton fabric, and the printed fabric obtained is dried and steamed at 102° C. in saturated steam in the course of 2 minutes. The printed fabric is then rinsed, optionally soaped off at the boil and rinsed once more, and then dried.

PRINTING METHOD II 5 parts of the reactive dye obtained as described in Example 1 are sprinkled with rapid stirring into 100 parts of stock thickening containing 50 parts of 5% sodium alginate solution, 36.5 parts of water, 10 parts of urea, 1 part of sodium m-nitrobenzenesulfonate and 2.5 parts of sodium bicarbonate. The print paste thus obtained, the stability of which meets industrial requirements, is used to print a cotton fabric, and the printed fabric obtained is dried and steamed at 102° C. in saturated steam in the course of 8 minutes. The printed fabric is then rinsed, optionally soaped off at the boil and rinsed once more, and then dried.

What is claimed is:

1. A compound of the formula

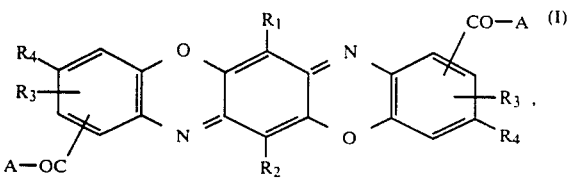

wherein $R_1$ and $R_2$ are each independently of the other hydrogen, halogen, $C_1$-$C_4$alkyl, $C_1$-$C_4$alkoxy, phenoxy, carboxyl, carbamoyl or $C_1$-$C_4$alkanoylamino; $R_3$ is hydrogen, sulfo, $C_1$-$C_4$alkoxy, halogen, carboxyl, carbamoyl, N—$C_1$-$C_4$alkylcarbamoyl, N,N—di—$C_1$-$C_4$alkylcarbamoyl, $C_1$-$C_4$alkylsulfonyl, sulfamoyl, N—$C_1$-$C_4$alkylsulfamoyl or N,N—di—$C_1$-$C_4$alkylsulfamoyl; $R_4$ is a radical of the formula

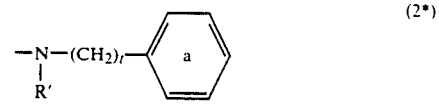

$R_5$ and $R_6$ are independently of each other hydrogen or unsubstituted or hydroxyl-, sulfo-, sulfato-, carboxyl-, cyano-, halogen-, $C_1$-$C_4$alkoxycarbonyl-, $C_1$-$C_4$alkanoyloxy- or carbamoyl-substituted and uninterrupted or, except in the case of methyl, —O—, —S— or -NH- interrupted $C_1$-$C_6$alkyl; R' is hydrogen or $C_1$-$C_6$alkyl; t is an integer from 0 to 4; the phenyl radical (a) is unsubstituted or substituted by $C_1$-$C_4$alkyl, $C_1$-$C_4$alkyl substituted by hydroxyl-, sulfo or sulfato, $C_1$-$C_4$alkoxy, halogen, sulfo, carboxyl or hydroxy, and A is a radical of the formula

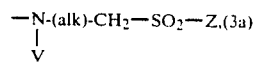

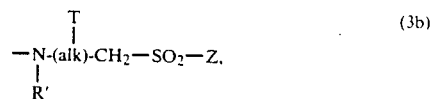

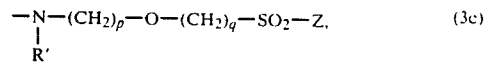

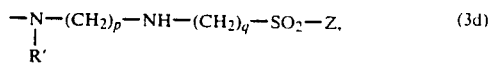

-continued

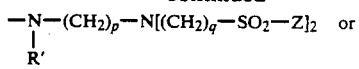 (3e)

or

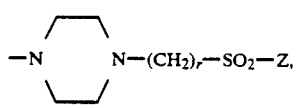 (3f)

where R' is as defined above, (alk) is $C_1$-$C_6$alkylene, T is hydrogen, halogen, hydroxyl, sulfato, carboxyl, cyano, $C_1$-$C_4$alkanoyloxy, $C_1$-$C_4$alkoxycarbonyl, carbamoyl or a radical —$SO_2$—Z, V is hydrogen, unsubstituted $C_1$-$C_4$alkyl, $C_1$-$C_4$alkyl substituted by halogen, hydroxyl, cyano, carboxyl, sulfo, sulfato, $C_1$-$C_4$alkoxy or $C_1$-$C_4$alkoxycarbonyl or V is a radical of the formula —(alk)—$CH_2$—$SO_2$—Z, where (alk) is as defined above, Z is a radical of the formula —CH=$CH_2$ or —$CH_2$—$CH_2$—Y, Y is a leaving group selected from the group consisting of —$OSO_3H$, —$SSO_3H$, —O-$COCH_3$, —OCO—$C_6H_5$, $OPO_3H_2$, —Cl, Br, —F,

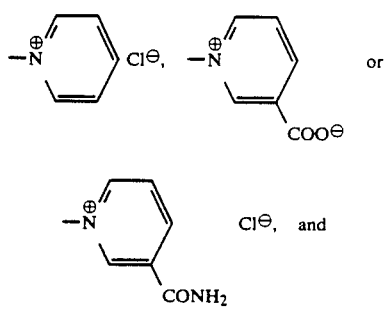

p, q and r are each independently of the others an integer from 1 to 6.

2. A compound according to claim 1, wherein $R_1$ and $R_2$ are each hydrogen, methyl, methoxy, acetylamino or chlorine and $R_3$ is hydrogen, chlorine, $C_1$-$C_4$alkyl or $C_1$-$C_4$alkoxy.

3. A compound according to claim 2, wherein $R_1$ and $R_2$ are each chlorine and $R_3$ is hydrogen.

4. A compound according to claim 1, wherein $R_4$ is a radical of the formula $$\begin{array}{c} R' \\ | \\ -N\text{-alk-U}, \end{array} \quad (2a)$$

—N[(alk)-U]$_2$, (2b)

—NH—($CH_2$)$_p$—O—($CH_2$)$_q$—U, (2c)

—NH—($CH_2$)$_p$—NH—($CH_2$)$_q$—U or (2d)

$$\begin{array}{c} U \\ | \\ -NH-(CH_2)\text{-(alk)-}CH_2-U \end{array} \quad (2e)$$

where U is hydroxyl, sulfo, sulfato, carboxyl, cyano, halogen, $C_1$-$C_4$alkoxycarbonyl, $C_1$-$C_4$alkanoylamino or carbamoyl.

5. A compound according to claim 1, wherein $R_4$ is a radical of the formula $$\begin{array}{c} R'' \\ | \\ -N\text{-(alk')-U'}, \end{array} \quad (2a')$$

—N[(alk')-U']$_2$, (2b')

—NH—$CH_2$—$CH_2$—O—$CH_2$—$CH_2$—U', (2c')

—NH—$CH_2$—$CH_2$—NH—$CH_2$—$CH_2$—U' or (2d')

$$\begin{array}{c} -NH-CH_2\text{-(alk')-}CH_2-U' \\ | \\ U' \end{array} \quad (2e')$$

where R'' is hydrogen, methyl or ethyl, (alk') is $C_1$-$C_4$alkylene and U' is hydroxyl, sulfo or sulfato.

6. A compound according to claim 1, wherein $R_4$ is a radical of the formula (2*) indicated in claim 1, R' is hydrogen, t is 1 or 2 and the phenyl radical (a) is unsubstituted or sulfo-, methyl- or methoxy-substituted.

7. A compound according to claim 1, wherein the leaving group Y is a radical —$OSO_3H$, —$SSO_3H$, —O-$COCH_3$, —OCO—$C_6H_5$, $OPO_3H_2$, —Cl, —Br, —F,

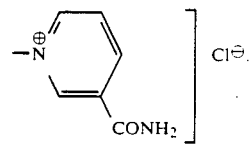

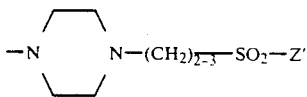

8. A compound according to claim 1, wherein the leaving group Y is a radical —$OSO_3H$, —$SSO_3H$, —O-$COCH_3$, —$OPO_3H_2$ or —Cl.

9. A dye of claim 8 wherein Y is —$OSO_3$—H.

10. A compound according to claim 1, wherein A is a radical of the formula $$\begin{array}{c} -N\text{-(alk')-}CH_2-SO_2-Z', \\ | \\ V' \end{array} \quad (3a')$$

$$\begin{array}{c} SO_2-Z' \\ | \\ -NH\text{-(alk')-}CH_2-SO_2-Z', \end{array} \quad (3b')$$

—NH—$CH_2$—$CH_2$—O—$CH_2$—$CH_2$—$SO_2$—Z', (3c')

—NH—$CH_2$—$CH_2$—NH—$CH_2$—$CH_2$—$SO_2$—Z' or (3d')

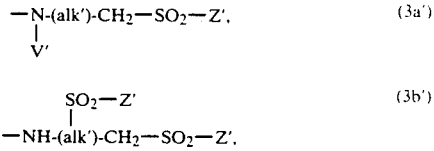 (3f)

where V' is hydrogen, methyl, ethyl or a radical —(alk')—$CH_2$—$SO_2$—Z', (alk') is $C_1$-$C_4$alkylene, Z' is vinyl or —$CH_2$—$CH_2$—Y', and Y' is —$OSO_3H$, —$SSO_3H$, —$OCOCH_3$, —$OPO_3H_2$ or —Cl.

11. A compound according to claim 1, wherein A is a radical of the formula

—NH—($CH_2$)$_2$—$SO_2$—($CH_2$)$_2$—$OSO_3H$,

—NH—($CH_2$)$_3$—$SO_2$—($CH_2$)$_2$—$OSO_3H$,

—NH—($CH_2$)$_2$—O—($CH_2$)$_2$—$SO_2$—($CH_2$)$_2$—$OSO_3H$.

-continued $-N[(CH_2)_2-SO_2-(CH_2)_2-OSO_3H]_2,$ $-\underset{\underset{CH_3}{|}}{N}-(CH_2)_2-SO_2-(CH_2)_2-OSO_3H,$ $-\underset{\underset{C_2H_5}{|}}{N}-(CH_2)_2-SO_2-(CH_2)_2-OSO_3H,$ $-NH-CH_2-\underset{\underset{SO_2-(CH_2)_2-OSO_3H}{|}}{CH}-CH_2-CH_2-CH_2-SO_2-(CH_2)_2-OSO_3H$ or

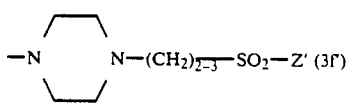 $N-(CH_2)_3-SO_2-(CH_2)_2-OSO_3H.$

12. A compound of the formula (1) according to claim 1 wherein $R_1$ and $R_2$ are each chlorine, $R_3$ is hydrogen, $R_4$ is a radical of the formula $-\underset{\underset{}{\overset{R'}{|}}}{N}\text{-alk-U},$ (2a)

$-N[(alk)-U]_2,$ (2b)

$-NH-(CH_2)_p-O-(CH_2)_q-U,$ (2c)

$-NH-(CH_2)_p-NH-(CH_2)_q-U$ or (2d)

$-NH-(CH_2)-(alk)-\underset{\underset{}{\overset{U}{|}}}{CH_2}-U$ (2e)

where U is hydroxyl, sulfo, sulfato, carboxyl, cyano, halogen, $C_1$-$C_4$alkoxycarbonyl, $C_1$-$C_4$alkanoylamino or carbamoyl and A is a radical of the formula $-\underset{\underset{V'}{|}}{N}\text{-(alk')-}CH_2-SO_2-Z',$ (3a')

$-NH\text{-(alk')-}\underset{\underset{}{\overset{SO_2-Z'}{|}}}{CH_2}-SO_2-Z',$ (3b')

$-NH-CH_2-CH_2-O-CH_2-CH_2-SO_2-Z',$ (3c')

$-NH-CH_2-CH_2-NH-CH_2-CH_2-SO_2-Z'$ or (3d')

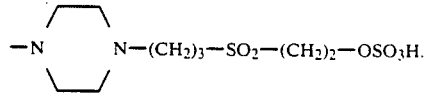 $N-(CH_2)_{2-3}-SO_2-Z'$ (3f')

where V' is hydrogen, methyl, ethyl or a radical -(alk')-$CH_2$-$SO_2$-Z', (alk') is $C_1$-$C_4$ alkylene, Z' is vinyl or $-CH_2-CH_2-Y'$, and Y' is $-OSO_3H$, $-SSO_3H$, $-OCOCH_3$, $-OPO_3H_2$ or $-Cl$.

13. A compound of the formula (1) according to claim 1 wherein $R_1$ and $R_2$ are each chlorine, $R_3$ is hydrogen, $R_4$ is a radical of the formula $-\underset{\underset{}{\overset{R''}{|}}}{N}\text{-(alk')-U'},$ (2a')

$-N[(alk')-U']_2,$ (2b')

$-NH-CH_2-CH_2-O-CH_2-CH_2-U',$ (2c')

$-NH-CH_2-CH_2-NH-CH_2-CH_2-U'$ or (2d')

$-NH-CH_2\text{-(alk')-}\underset{\underset{U'}{|}}{CH_2}-U'$ (2e)

where R" is hydrogen, methyl or ethyl, (alk') is $C_1$-$C_4$alkylene and U is hydroxyl, sulfo or sulfato and A is a radical of the formula $-NH-(CH_2)_2-SO_2-(CH_2)_2-OSO_3H,$ $-NH-(CH_2)_3-SO_2-(CH_2)_2-OSO_3H,$ $-NH-(CH_2)_2-O-(CH_2)_2-SO_2-(CH_2)_2-OSO_3H,$ $-N[(CH_2)_2-SO_2-(CH_2)_2-OSO_3H]_2,$ $-\underset{\underset{CH_3}{|}}{N}-(CH_2)_2-SO_2-(CH_2)_2-OSO_3H,$ $-\underset{\underset{C_2H_5}{|}}{N}-(CH_2)_2-SO_2-(CH_2)_2-OSO_3H,$ $-NH-CH_2-\underset{\underset{SO_2-(CH_2)_2-OSO_3H}{|}}{CH}-CH_2-CH_2-CH_2-SO_2-(CH_2)_2-OSO_3H$ or

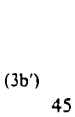 $N-(CH_2)_3-SO_2-(CH_2)_2-OSO_3H.$

14. A compound of the formula (1) according to claim 1, wherein $R_1$ and $R_2$ are each chlorine, $R_3$ is hydrogen, $R_4$ is a radical of the formula (2*), where R' is hydrogen, t is 1 or 2, the phenyl radical (a) is unsubstituted or sulfo-, methyl- or methoxy-substituted, and A is $-NH-(CH_2)_2-SO_2-(CH_2)_2-OSO_3H,$ $-NH-(CH_2)_3-SO_2-(CH_2)_2-OSO_3H,$ $-NH-(CH_2)_2-O-(CH_2)_2-SO_2-(CH_2)_2-OSO_3H,$ $-N[(CH_2)_2-SO_2-(CH_2)_2-OSO_3H]_2,$ $-\underset{\underset{CH_3}{|}}{N}-(CH_2)_2-SO_2-(CH_2)_2-OSO_3H,$ $-\underset{\underset{C_2H_5}{|}}{N}-(CH_2)_2-SO_2-(CH_2)_2-OSO_3H,$ $-NH-CH_2-\underset{\underset{SO_2-(CH_2)_2-OSO_3H}{|}}{CH}-CH_2-CH_2-CH_2-SO_2-(CH_2)_2-OSO_3H$ or

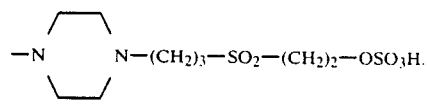 $N-(CH_2)_3-SO_2-(CH_2)_2-OSO_3H.$

* * * * *